US008545543B2

(12) United States Patent
Zorzos et al.

(10) Patent No.: US 8,545,543 B2
(45) Date of Patent: Oct. 1, 2013

(54) METHODS AND APPARATUS FOR MICROSTRUCTURE LIGHTGUIDES

(75) Inventors: Anthony Zorzos, Cambridge, MA (US); Clifton Fonstad, Arlington, MA (US); Edward Boyden, Chestnut Hill, MA (US); Jacob Bernstein, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 368 days.

(21) Appl. No.: 12/843,587

(22) Filed: Jul. 26, 2010

(65) Prior Publication Data

US 2011/0087311 A1   Apr. 14, 2011

Related U.S. Application Data

(60) Provisional application No. 61/249,714, filed on Oct. 8, 2009.

(51) Int. Cl.
*A61N 5/06* (2006.01)
*A61N 5/067* (2006.01)
*G02B 6/10* (2006.01)

(52) U.S. Cl.
USPC ............... 607/89; 607/93; 385/129; 385/130; 385/131

(58) Field of Classification Search
USPC .............................. 607/89, 93; 385/129–131
See application file for complete search history.

(56) References Cited

U.S. PATENT DOCUMENTS

| | | | | |
|---|---|---|---|---|
| 3,784,386 A | * | 1/1974 | Araujo et al. | 501/13 |
| 2002/0009603 A1 | * | 1/2002 | McGill et al. | 428/447 |
| 2003/0072524 A1 | * | 4/2003 | Kang et al. | 385/31 |
| 2003/0091289 A1 | * | 5/2003 | Saito et al. | 385/49 |
| 2003/0176002 A1 | * | 9/2003 | Zhang et al. | 438/22 |
| 2009/0210039 A1 | | 8/2009 | Boyden et al. | |
| 2009/0221921 A1 | * | 9/2009 | Cottrell et al. | 600/478 |

OTHER PUBLICATIONS

Bernstein et al. "Prosthetic systems for therapeutic optical activation and silencing of genetically targeted neurons," May 2008, NIH Public Access Author Manuscripts, pp. 1-16.*
Poher, V., Grossman, N., Kennedy, G., Nikolic, K., Zhang, H., Gong, Z., et al. (2008). Micro-LED arrays: a tool for two-dimensional neuron stimulation. 2008 Journal of Physics D: Applied Physics 41, 094014.
Xu, H., Zhang, J., Davitt, K., Song, Y., & Nurmikko, A. (2008). Application of blue-green and ultraviolet micro-LEDs to biological imaging and detection. Journal of Physics D: Applied Physics 41 094013.

* cited by examiner

*Primary Examiner* — Jessica Stultz
*Assistant Examiner* — Michael Carter
(74) *Attorney, Agent, or Firm* — Stephen R. Otis (57) ABSTRACT

This invention may be implemented as a microstructure probe for delivering light of variable color and/or power, via a set of integrated lightguides, from an optical source (or set of sources) to regions spatially arranged 3-dimensionally, with a length scale of microns to millimeters. In exemplary embodiments of this invention, a microstructure probe comprises many lightguides and is adapted to be inserted into neural or other tissue. The lightguides run in parallel along at least a portion of the axis of the probe. The probe may deliver light to many points along the axis of insertion of the probe. This invention may be implemented as an array of two or more such probes (each of which comprises multiple lightguides). This array may be used to deliver light to neural tissue in a complex 3D pattern.

19 Claims, 6 Drawing Sheets

METHODS AND APPARATUS FOR MICROSTRUCTURE LIGHTGUIDES

RELATED APPLICATION

This application claims the benefit of U.S. Provisional Application Ser. No. 61/249,714, filed Oct. 8, 2009, the entire disclosure of which is incorporated by reference herein.

STATEMENT REGARDING FEDERALLY SPONSORED RESEARCH OR DEVELOPMENT

This invention was made with U.S. government support under Grant No. DGE0645960 awarded by the National Science Foundation and under Grant Nos. OD002002 and DA029639 awarded by the National Institutes of Health. The government has certain rights in this invention.

FIELD OF THE TECHNOLOGY

The present invention relates generally to waveguides.

BACKGROUND

A problem, in neuroscience, is how to deliver light in a complex, 3D pattern to different locations in a mammalian brain. A further problem is how to deliver light into different layers of neural tissue, in such a way that the light pulses are in a direction parallel to these layers.

Prior to this invention, neither could be done.

To understand why these problems are important, it is helpful to understand recent advances in phototherapy. Recently, optogenetic reagents have been used to facilitate optical control of neural circuits in mammalian brains. These reagents include channelrhodopsin-2 (ChR2), N. pharaonis halorhodopsin (Halo/NpHR), a variant of halorhodopsin, ss-Prl-Halo (sPHalo), an opsin (Arch) derived from an archaebacterium, and an opsin (Mac) derived from the fungus Leptosphaeria maculans. For example, a neuron that has been exposed to such a reagent may, upon exposure to a certain wavelength of light, be activated or silenced.

Many neural circuits in mammalian brains are 3-dimensional and geometrically complex. The ability to optically drive or silence neural activity in complexly-shaped brain circuits (such as the entire CA1 region of the hippocampus, the reticular nucleus of the thalamus, or a specific layer of frontal cortex), for milliseconds to seconds at a time, would be highly desirable.

A "lightguide" means an optical waveguide.

Prior to this invention, lightguides were able only to deliver light along a single pathway to a single location. They were not able to deliver light in 2D or 3D patterns to multiple locations, much less to deliver light to multiple layers of tissue in a direction parallel to these layers.

Some existing 2D arrays of light emitting diodes (LEDs) can produce light in 2D patterns. However, they suffer from a major disadvantage for neuroscience applications: the LEDs produce too much heat. When such an LED array is inserted into a mammalian brain, the heat from the LEDs interferes with neural function or its measurement, and may even harm neural tissue.

SUMMARY

This invention may be implemented as a microfabricated probe for delivering light of variable color and/or power, via a set of integrated lightguides, from an optical source (or set of sources) to regions spatially arranged 3-dimensionally, with a length scale of microns to millimeters. The geometry of this structure (e.g., its 3-dimensional layout, and the number and size of lightguides) is application dependent.

A "probe" comprises a slender or rodlike tool adapted for being inserted into another object.

In exemplary embodiments of this invention, a microstructure probe comprises many lightguides and is adapted to be inserted into neural or other tissue. The lightguides run in parallel along at least a portion of the axis of the probe. The thin probe may deliver light to many points along the axis of insertion of the probe. This design maximizes the flexibility and power of optical neural control while minimizing tissue damage.

This invention may be implemented as an array of two or more such probes (each of which comprises multiple lightguides). This array may be used to deliver light to neural tissue in a complex 3D pattern. (Indeed, even a single probe, by delivering light to multiple points along its axis, delivers light in a 3D pattern. By inserting an array of multiple probes, the three-dimensionality is enhanced.)

This invention may be implemented in such a way that at least some of the lightguides in a probe bend at a steep angle, for example 90°. A 90° bend region is too steep of an angle for internal reflection between two dielectrics to occur. To solve this problem, a thin mirrored metallic surface (e.g., about 50 nm thick) may deposited by e-beam deposition over the cladding of a lightguide, to reflect light that would otherwise escape steep angles. This ability to bend light at steep angles is advantageous in many contexts. For example, by bending the optical pathways of multiple lightguides, each by 90° at a point close to where the light exits the probe, light pulses may be delivered to multiple layers of tissue in a direction parallel to the planes of such layers and perpendicular to the axis of the probe.

In exemplary embodiments of this invention, a probe may deliver light of different colors or power. For example, a probe may include at least one merged waveguide, which comprises multiple light pipes that merge into a convergent light channel. An independent light source may be coupled with each such light pipe. These light sources may have different colors or intensity of light. Accordingly, the convergent channel may be used to deliver, to a single location, light that varies in color or intensity. Or, for example, even if each lightguide in a probe delivers only a single color of light, different lightguides in that probe may deliver different colors, so that the single probe may deliver different colors of light.

Here are some examples of how this invention may be implemented:

This invention may be implemented as apparatus comprising a plurality of microfabricated lightguides, which apparatus is adapted for: (a) being inserted into another object, and (b) delivering light to a plurality of locations at different depths along the axis of insertion of said apparatus. Furthermore: (1) the lightguides may comprise dielectric waveguides and the cladding of at least one lightguide may be coated, at least in part, by a metallic mirror layer; (2) the apparatus may further comprise a silicon substrate, (3) the core of at least one said lightguide may comprise $SiO_xN_y$ or SU-8, (4) the apparatus may be adapted to bend light in such a manner that, in at least one location, light exits the apparatus at an angle within 20 degrees of perpendicular to the axis of insertion of the apparatus, (5) the apparatus may be adapted to deliver light in such a manner that the color of light delivered to a location at a particular time differs from the color of light delivered to the same location at a different time, and (6) at least one said probe may be implemented so that its maximum thickness, measured in any direction perpendicular to its axis of insertion, does not exceed 550 microns.

This invention may be implemented as apparatus comprising a plurality of probes, wherein: (a) each probe comprises a plurality of lightguides, (b) each probe is adapted for delivering light from multiple light sources to multiple locations, and (c) the apparatus is adapted for delivering light to multiple points in a three-dimensional pattern. Furthermore: (1) at least one such light source may be adapted to produce light that differs in color or intensity or both, from light produced by another such light source, and (2) the apparatus may be adapted to deliver light to multiple locations in a three-dimensional arrangement in such a way that the color of light delivered to at least one location differs from the color of light delivered to at least one other location.

This invention may be implemented as apparatus comprising a plurality of lightguides, wherein the lightguides are adapted: (a) to be inserted into tissue, and (b) to deliver light to multiple locations in such a way that at least one lightguide outputs light that differs, in color or intensity or both, from light that is outputted by at least one other lightguide. Furthermore: (1) the apparatus may further comprise a plurality of light sources positioned in such a manner that, for some or all of said light sources, each light source is aligned with the input of a lightguide, (2) the apparatus may be adapted to receive light from multiple external light sources, (3) the apparatus may be adapted to receive light from at least one external light source, and (4) the cladding of at least one said lightguide may comprise $SiO_2$.

This invention may be implemented as a process that comprises using an insertable probe comprising a plurality of lightguides to send light to a plurality of locations at different depths along the axis of insertion of said probe. Furthermore: (1) at least some of the light may be produced by at least one laser, (2) at least some of the light may be produced by at least one LED, and (3) at least one such lightguide may comprise a dielectric waveguide.

DETAILED DESCRIPTION

This invention may be implemented as a microstructure probe for delivering light of variable color or power, via a set of integrated lightguides, from an optical source (or set of sources) to regions spatially arranged 3-dimensionally, with length scale of microns to millimeters. The geometry of this structure (e.g., its 3-dimensional layout, and the number and size of lightguides) is application dependent.

Figure 1:
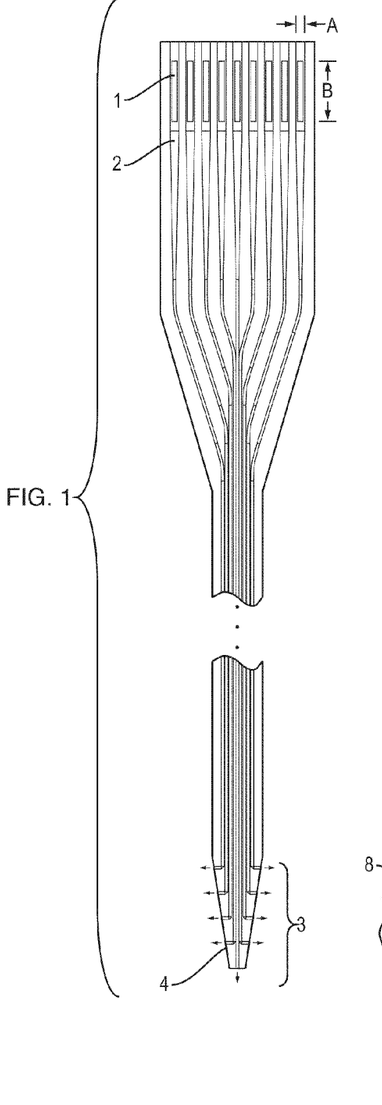
FIG. 1 is a schematic of a probe comprised of multiple lightguides, in a working prototype of this invention.

According to principles of this invention, multiple lightguides may be integrated into a single probe. FIG. 1 is a schematic of the head and needle ends of a probe, in an illustrative implementation of this invention. The probe comprises nine laser inputs, which send light into nine lightguides that terminate at different depths along the axis of the probe, allowing light delivery to different depths along the axis of the probe. The lightguides run parallel (or roughly parallel) to each other in portions of the head and needle end of the probe. In this example, the input for each lightguide is a ridge guide micro-platelet laser (such as the laser at (1)). Each lightguide (such as the lightguide at (2)) is about 60 microns wide (A) near the input and tapers to about 20 microns wide for most of its length. The length of each laser is about 300 microns (B). Near the tip of the needle end of the probe, the lightguides terminate at different depths (3). Some of the lightguides bend about 90% near where the light exits the probe (such as the bend at (4)). Thus, light exits the probe at multiple points in multiple directions.

In practice, the number of lightguides in a probe may be much higher than nine. For example, a probe may have 20 to 50 channels of light.

Figure 2:
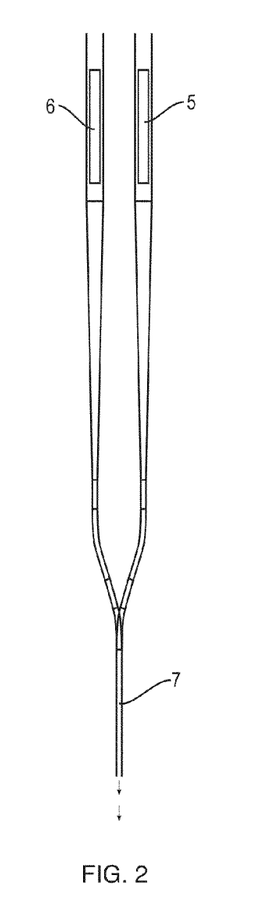
FIG. 2 is a schematic of a lightguide that delivers pulses of two different colors of light, in a working prototype of this invention.

FIG. 2 is a schematic of a structure that joins two waveguides into one, for delivery of multiple colors (e.g., yellow and blue) of light from a single output port, in an illustrative implementation of this invention. For example, in FIG. 2, laser (5) may produce light that differs in color and/or intensity from the light produced by laser (6). When either of these lasers pulse light, the light travels down the respective light pipe and into a single convergent channel 7 and then exits from the output port.

The same approach may be used to merge more than two waveguides into a single convergent channel. These merged waveguides allow different colors (and/or different intensities) of light produced by multiple independent lasers to be delivered to a single point in the brain.

Together, the lightguides shown in FIGS. 1 and 2 allow delivery light of multiple colors, to arbitrary locations along the axis of a probe.

Figure 3:
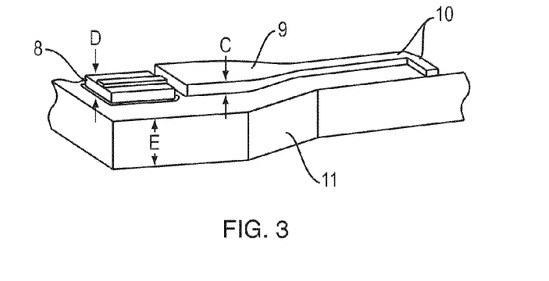
FIG. 3 is a perspective view of a laser diode coupled to a probe, in an illustrative implementation of this invention.

FIG. 3 is a perspective sketch of a ridge guide microcleaved platelet laser diode (8) aligned with the input of a multi-mode rectangular dielectric lightguide (9) and bonded on a contact pad, in an illustrative implementation of this invention. In this embodiment, the laser (8) is about 5 microns thick (D); the lightguide is about 10 microns thick (C), and the silicon substrate (11) is about 150 microns thick (E) These dimensions vary in different embodiments, but give a sense the micro-scale assembly and integration that may be used for the light-guide probe. In FIG. 3, the body and needle end (10) of the lightguide are also shown. However, they are not drawn to scale. In a typical embodiment, the body and needle end (10) of the probe would be much longer (relative to the head of the lightguide) than shown in FIG. 3.

In illustrative embodiments of this invention, the lightguides that guide light down the probe comprise a "core" material surrounded by a "cladding" material. In some embodiments, the core material is SU-8 (a polymeric negative photoresist). In some others, the core material is a silicon oxy-nitride, $SiO_xN_y$. For both of these core materials, the surrounding cladding material may be silicon dioxide, $SiO_2$.

Figure 4:
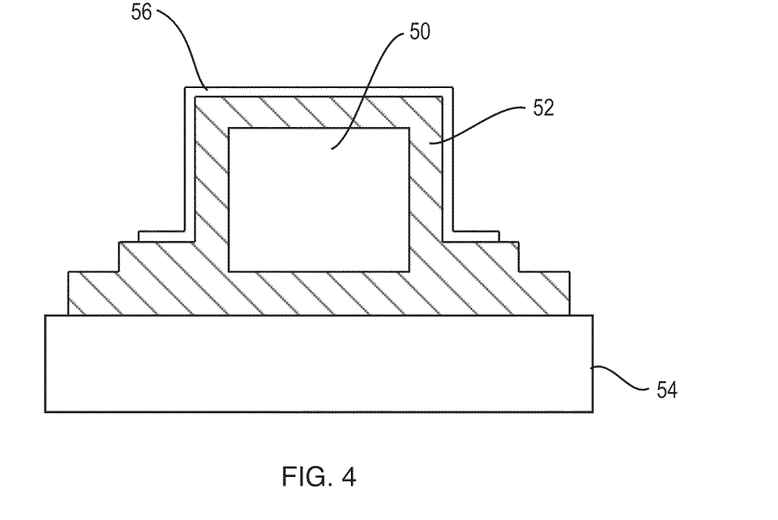
FIG. 4 shows a cross-section of a lightguide with an SU-8 core, in an illustrative implementation of this invention.

FIG. 4 is a cross-section view of a lightguide with an SU-8 core, in an illustrative implementation of this invention. In this example, the SU-8 core (50) is about 50 microns thick, the $SiO_2$ cladding (52) is about 3 microns thick, and the silicon substrate (54) is about 650 microns thick.

Figure 5:
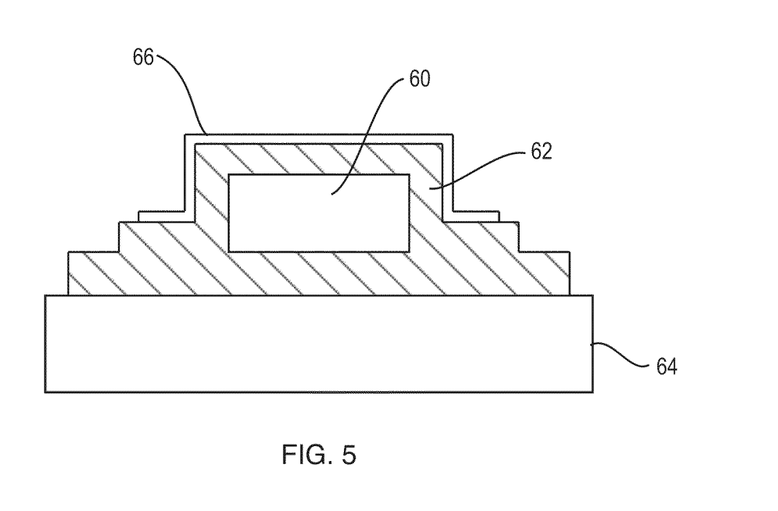
FIG. 5 shows a cross-section of a lightguide with an $SiO_xN_y$ core, in an illustrative implementation of this invention.

FIG. 5 is a cross-section view of a lightguide with an $SiO_xN_y$ core, in an illustrative implementation of this invention. In this example, the $SiO_xN_y$ core (60) is about 10 microns thick, the $SiO_2$ cladding (62) is about 3 microns thick, and the silicon substrate (64) is about 650 microns thick.

In the examples shown in FIGS. 4 and 5, an aluminum layer (56) (66) that is about 50 nm thick is used to reflect light that goes through the cladding, important for steering corners and similar sharp changes in bend angle. In this example, the aluminum layer was added using e-beam deposition.

In illustrative implementations of this invention (including the examples shown in FIGS. 4 and 5), the lightguides are dielectric waveguides that rely on internal reflection between two dielectrics. In that case, an important consideration is the difference in the indices of refraction between the core and cladding. All parameters equal, the larger the "index step," the larger the transmission for any given waveguide geometry. Therefore, any two materials, one with a higher index of refraction and the other with a lower index of refraction, can serve as core and cladding respectively, assuming the optical transparency is sufficient.

However, this invention is not limited to dielectric waveguides, but may be implemented with other types of waveguides, such as photonic-crystal fiber, or hollow tubes coated with a reflective inner surface.

The overall arrangement of the probe is customizable, based on the needs of the particular application. In FIG. 1, a probe delivers light with axial variability to the lateral sides of the probe shaft. However, this invention may be implemented to deliver light to an arbitrary arrangement of illumination points: laterally, backside, frontside, low resolution, high resolution, large or small illumination regions, etc. Two limiting factors for the probe arrangement are: (1) lithographic resolution, and (2) optical loss. The line-width of the guide channels is limited by the available lithographic system being used to shape the core material. In an illustrative embodiment, the probe is made with a standard microfabrication UV-alignment exposure system; however, other lithographic systems can be used and have inherent spatial limitations.

Although there is flexibility in selecting the selecting the arrangement of the lightguide, an important issue is transmission efficiency: some arrangements yield lower transmission coefficients.

Consider dielectric waveguides that rely on internal reflection between two dielectrics. Examples of such waveguides are shown in FIGS. 4 and 5. For such a waveguide, the higher the index step between the core and cladding, the more efficiently the light will be "confined" to the core. Also, the higher the transparency of the core material, the less light will be absorbed or scattered, yielding a higher transmission. Also, the less the bend curvature, the more efficient the transmission is.

In some instances, it is desirable to have sharp bend in a light guide, even though it reduces or eliminates the transmission that may be achieved by internal reflection. In other words, it may be desirable to locally abandon internal reflection in order to achieve high resolution output. For example, a 90° bend in a lightguide, near the point where the light exits the probe, may be desirable in order to shine light in a direction parallel to a tissue layer and perpendicular to the axis of the probe. But a 90° bend region is far too steep of an angle for internal reflection to occur. This is why, as shown in the cross sections of FIGS. 4 and 5, a thin (50 nm) mirrored metallic surface may be deposited over the cladding, to reflect light which would otherwise escape steep angles. In some working prototypes, aluminum was used as the metal and applied over the cladding of the entire shank of the probe, using sputter deposition. Alternately, the metal may be deposited just locally at and near a steep bend in a lightguide.

If a lightguide is not a dielectric waveguide, then the factors that impact transmission efficiency may be different.

FIGS. 6-10 are photomicrographs of lightguides with SU-8 cores in working prototypes of this invention.

Figure 6:
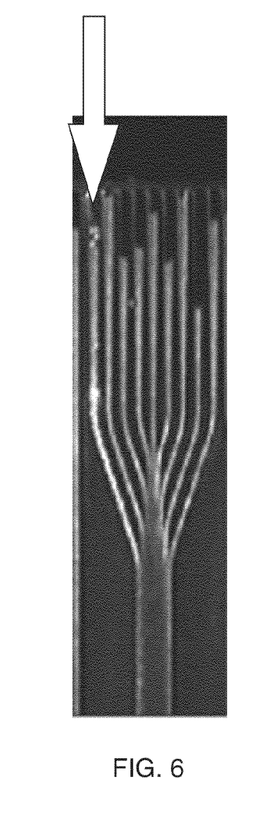
FIG. 6 is a photomicrograph taken in ambient light of a probe with nine lightguides, in a working prototype of this invention. The probe is the same as the one schematized in FIG. 1.
Figure 7:
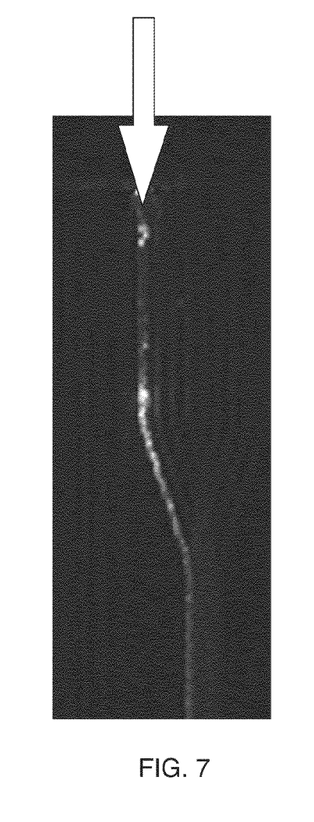
FIG. 7 is a photomicrograph of the same probe taken in a dark room, showing light being guided down a single lightguide in the probe, in a working prototype of this invention.

FIG. 6 is a photomicrograph taken in ambient light of a probe with nine lightguides. The probe is the same as the one schematized in FIG. 1. FIG. 7 is a photomicrograph of the same probe taken in a dark room, with the second lightguide from the left being illuminated. Scattered light can be seen in one section, showing selective guiding of light down one lightguide and not others.

Figure 8:
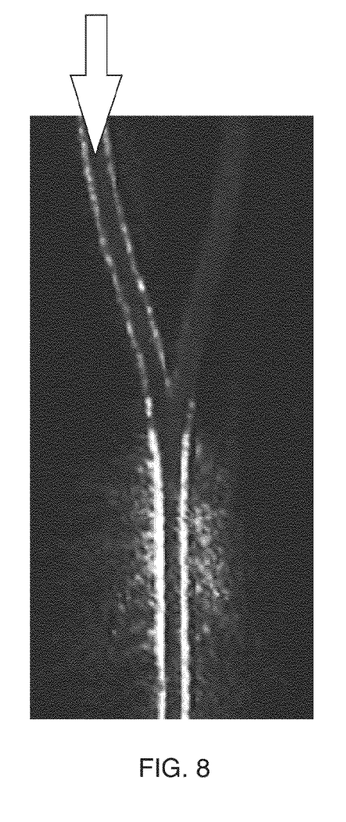
FIG. 8 is a photomicrograph of light shining down the left light pipe of a lightguide, in a working prototype of this invention.
Figure 9:
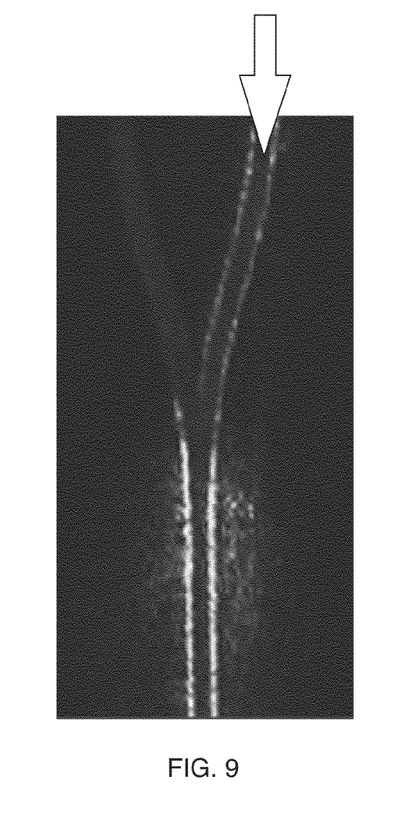
FIG. 9 is a photomicrograph of light shining down the right light pipe of the same lightguide, in a working prototype of this invention.
Figure 10:
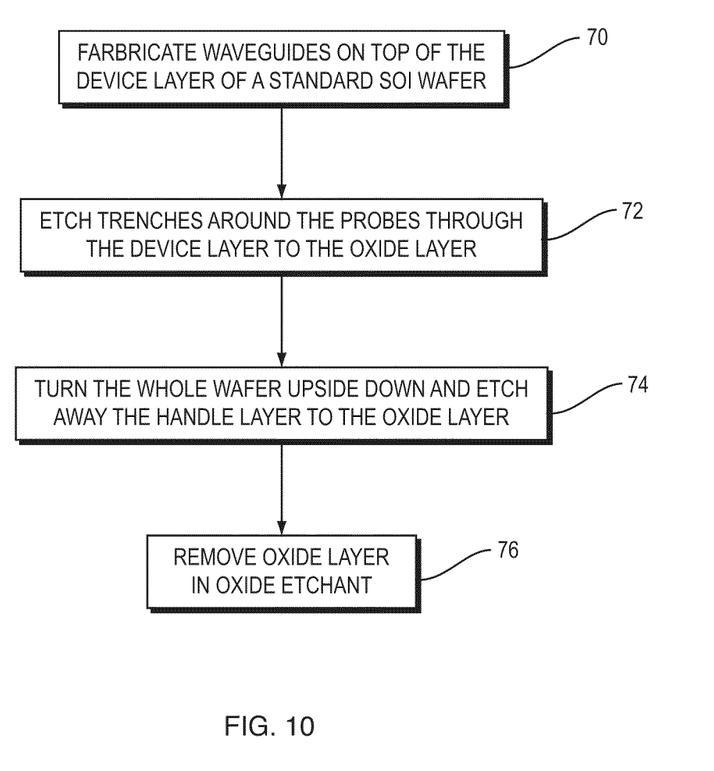
FIG. 10 is a flow chart of a steps used to 50 micron thick device layer using an SOI wafer, in a working prototype of this invention.

FIGS. 8 and 9 are microphotographs of a merged lightguide comprising two waveguides that converge into one. Such an arrangement is schematized in FIG. 2. In FIG. 8, a laser is shining down the left light pipe and light is observed going down the common convergent channel. In FIG. 9, a laser is shining down the right light pipe and light is again observed going down the common convergent channel. The merged lightguide shown in FIGS. 8 and 9 may be used to guide light from two independent light sources (that produce different colors of light) to the same point in the brain.

As shown in FIGS. 8 and 9, a single merged lightguide may deliver different colors of light. However, even if each lightguide in a probe delivers only a single color of light, different lightguides in that probe may deliver different colors, so that the single probe may deliver different colors of light.

This invention may be implemented as an array of two or more probes (each of which comprises multiple lightguides). Such an array may be used to deliver light to neural tissue in a complex 3D pattern. Even a single probe, by delivering light to multiple points along its axis, delivers light in a 3D pattern. By inserting an array of multiple probes, however, the three-dimensionality is enhanced. For example, lightguides may be arrayed on a circuit board.

In some embodiments of this invention, lightguides and light sources (e.g., laser diodes) are integrated with a silicon substrate. Silicon is desirable for many reasons, including its ease of use in microfabrication and mechanical rigidity. However, in some applications such as cochlear implants, mechanical rigidity is not desirable. In that case, a flexible core material (such as SU-8) and a flexible cladding material (such as polytetrafluoroethylene, sold under the brand name Teflon®) may be used. The substrate, if it is rigid, may be released after microfabrication. Alternately, a semi-rigid device layer may be used in conjunction with a flexible core and flexible cladding. For example, a semi-rigid device layer may comprise chrome or an oxide.

Figure 11:
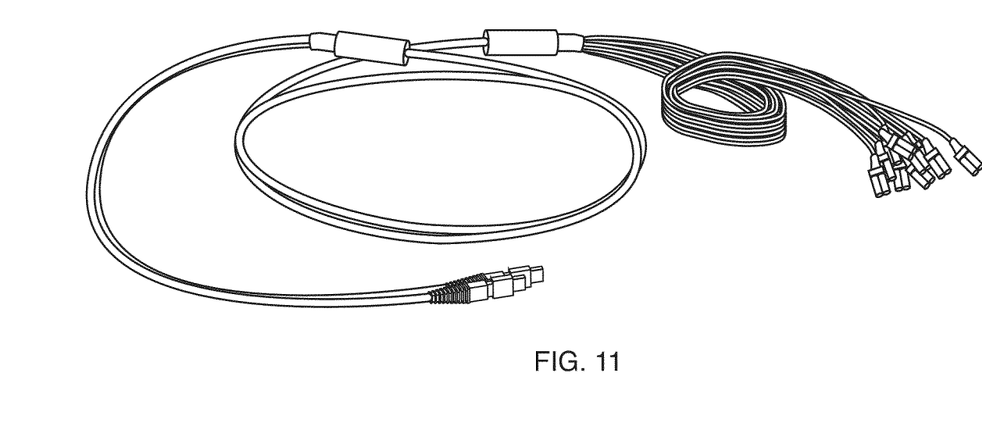
FIG. 11 shows a ribbon cable that may be used to deliver light pulses to a probe from one or more remote light sources, in an illustrative implementation of this invention.

A problem that confronted the inventors is how to make the device thinner, so that it causes less tissue damage when inserted. In early prototypes, the probes were fabricated on a standard 6 inch wide, 650 micron thick silicon wafer. The inventors attempted to reduce the thickness of the wafer, by polishing off the back of the wafer by abrasion. Unfortunately, in almost all cases, this damaged the probe. The inventors also tried to thin a 6 inch wide, 650 micron thick silicon wafer by laser-cutting the back of the wafer. However, laser cutting generates intense local heat, which may damage a probe The inventors eventually found that they could reduce the device thickness to 50 microns, by fabricating waveguides on a SOI (silicon on insulation) wafer with a 50 micron thick device layer, and then releasing. FIG. 11 is a flow chart that shows steps comprising that process. First, fabricate waveguides on top of the device layer of a standard SOI wafer (70). The SOI wafer comprises a thick bottom handle layer (silicon), a thin middle layer (oxide) and a thin (about 50 micron) top device layer (silicon). Second, etch trenches around the probes through the device layer to the oxide layer. (72) Third, turn the whole wafer upside down and etch away the handle layer to the oxide layer (74). Fourth, remove the oxide layer in the oxide etchant. (76) What is left, when this process is completed, is a thin isolated probe.

A variety of methods may be used to separate the probes from each other. For example, the device may be separated using a deep reactive ion etch (DRIE) tool, with a hard aluminum pattern used as a mask. Or, for example, laser cutting or chemical etching may be used.

This invention may be implemented with different types of independent light sources. Which light source is appropriate depends on factors such as the desired power and frequency of light, and the type of lightguide used in the probe. For example, in a probe with SU-8 core lightguides, a linear array of light emitting diodes (LED) may be butt-coupled to 50×60 µm lightguide inputs, one LED per lightguide input. The size and emission pattern of these LEDs is directly related to the coupling efficiency to the lightguides. For some neuroscience applications, the type of optogenetic molecular reagent being used determines the necessary emission frequency. There is a semi-continuous selection as to what frequency can be used with LED's, depending on the semiconductor material used.

For a probe with $SiO_xN_y$ core lightguides, LEDs are not desirable because the core material is so thin (about 10 µm) that high coupling efficiency cannot be achieved with an LED. However, an edge emitting laser diode may be coupled efficiently to this thin-film planar waveguide. The type of laser depends on the application. For example, blue laser diodes are of considerable interest in the field of optical neuromodulation. For applications needing a $SiO_xN_y$ core and efficient blue output, blue laser diodes may be butt-coupled to the lightguide inputs. LEDs and laser diodes are not an inclusive list of potential optical source candidates; they were simply chosen for ease, efficiency, and availability.

Figure 12:
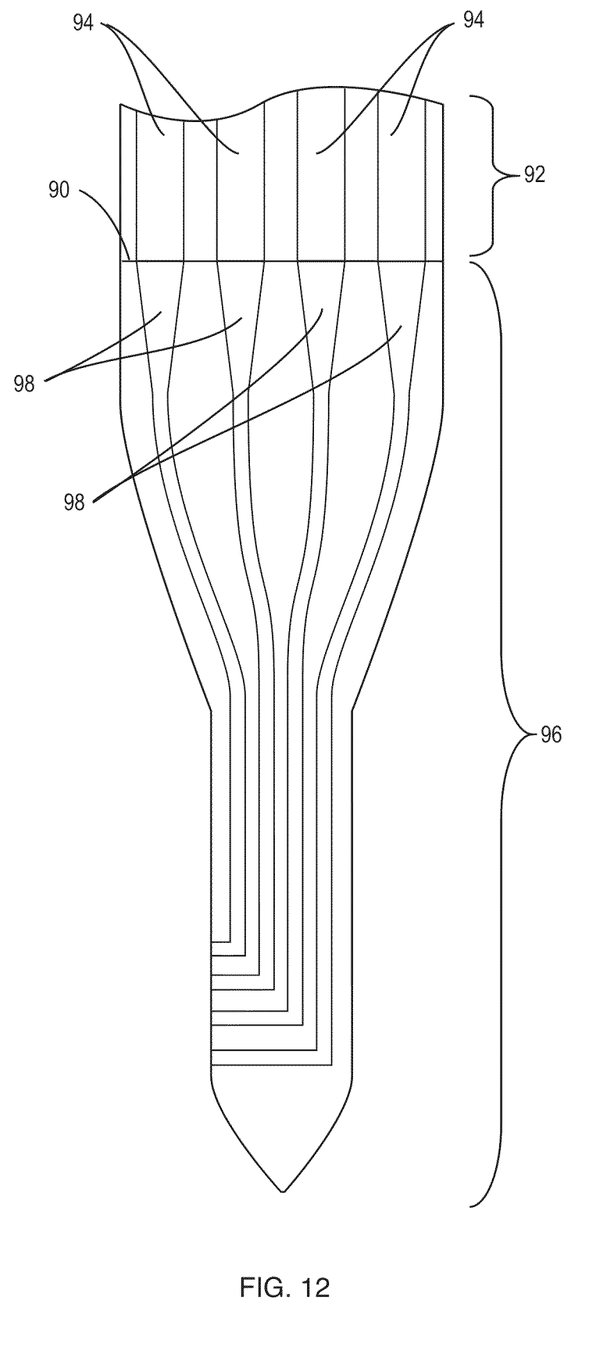
FIG. 12 is a schematic of strands of a multi-strand cable coupled to the inputs of lightguides, in an illustrative implementation of this invention.

A problem confronting the inventors was how to couple multiple independent light sources to lightguide inputs in a probe. As noted above, a light source (such as an LED or laser diode) may be butt-coupled to a lightguide input. However, in many applications, it is desirable to deliver light from remote, external light sources. In some embodiments of this invention, fiber-optic cables are used to deliver light from an external source. These cables are composed of a linear array of single-mode fiber-optics. They can be aligned and butt-coupled to a probe on one end and, on the other end, each fiber optic can individually be coupled to independent light source modules. For example, a 24 strand CABLExpress® Skinny-Trunk® ribbon cable, available from CXtec, Syracuse N.Y., may be used. FIG. 11 is a perspective sketch of such a ribbon cable. FIG. 12 is a schematic (not to scale) that shows an interface (90) between a cable and a probe, in an illustrative implementation of this invention. In this example, the cable (92) comprises four fiber optics (94). Each fiber optic is coupled to a lightguide (98) in the probe (96).

For some neuroscience applications involving molecular optogenetic reagents, a target output power for this device is greater than 200 mw/mm$^2$. However, this invention may be implemented with a variety of ranges of output power, depending on the application. For example, the output power may be 1 mW/mm$^2$ or 10 mW/mm$^2$ (which power levels are appropriate for some new reagents). The output power is dependent on factors such as: cladding/core material, index step, manner of guiding light, lightguide geometry, optical source power, optical source frequency, transmission efficiency, coupling efficiency, among others.

This invention may be implemented in such a way that the probe may also function as an electrode to record electrical activity. This may be achieved in a variety of ways. In some embodiments, an aluminum trace that coats the exterior (in order to capture light that would otherwise escape at steep angle) can be used for neural recording. Alternately, the waveguide itself can also be doped with conductive material, making it into an electrode. Or standard patterned electrodes, like "Michigan probes" (sold by NeuroNexus Technologies, Inc., Ann Arbor, Mich.), may be integrated into this structure along with the waveguides.

According to principles of this invention, an array of probes may deliver light of different colors and intensity to multiple points of a mammalian brain in a complex 3D pattern with great precision. This has important practical implications. For example, when used in conjunction with optogenetic reagents such as ChR2 and Halo, light may be used to activate or silence excitable cells (e.g., neurons, or heart muscle cells, brain cells, etc.) This ability to affect excitable cells may be used to advantage in the emerging field of phototherapy.

Conclusion

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:

1. Apparatus comprising a plurality of microfabricated lightguides, wherein:
    (a) the lightguides run along at least a portion of an elongated structure and terminate at different lengths along the elongated structure;
    (b) each of the lightguides, respectively, comprises a core material and a cladding material, the core material having a higher index of refraction than the cladding material;
    (c) within the elongated structure, each of at least some of the lightguides, respectively, changes direction at a bend, a mirrored metallic surface being adjacent to the cladding at the bend.

2. The apparatus of claim 1, wherein the bend is at a 90 degree angle.

3. The apparatus of claim 1, wherein the bend is at an angle too sharp for transmission of light by internal reflection between the core material and cladding material.

4. The apparatus of claim 1, wherein the metallic surface is configured to steer light that passes through the cladding at the bend.

5. The apparatus of claim 1, wherein said apparatus is adapted to bend light in such a manner that, in at least one location, light exits said apparatus at an angle within 20 degrees of perpendicular to the axis of insertion of said apparatus.

6. The apparatus of claim 1, wherein said apparatus is adapted to deliver light in such a manner that the color of light delivered to a location at a particular time differs from the color of light delivered to the same location at a different time.

7. The apparatus of claim 1, wherein the maximum thickness of at least one said probe, measured in any direction perpendicular to said axis of insertion, does not exceed 550 microns.

8. The apparatus of claim 1, wherein the metallic surface comprises aluminum.

9. The apparatus of claim 1, wherein the core material comprises SU-8.

10. A process that comprises using an insertable probe comprising a plurality of lightguides to send light to a plurality of locations in tissue at different depths along the axis of insertion of said probe, wherein:
 (a) each of at least some lightguides, out of the plurality of lightguides, changes direction at a bend, a mirrored metallic surface being adjacent to the bend; and
 (b) for each of the at least some lightguides, the process further includes using the mirrored metallic surface to steer light at the bend.

11. The process of claim 10, wherein the bend is at an angle too sharp for transmission of light by internal reflection between two dielectrics.

12. The process of claim 10, further comprising transmitting light from two different lasers at different times through two different lightguides, which two different lightguides converge into a single lightguide, which single lightguide is one of the plurality of lightguides.

13. The process of claim 10, wherein the process further comprises using the metallic surface as an electrode for neural recording.

14. The process of claim 10, wherein the process further comprises delivering light to multiple locations in such a way that at least one said lightguide outputs light that differs, in color or intensity or both, from light that is outputted by at least one other said lightguide.

15. The process of claim 10, wherein the probe is included in an array of probes, and the process further includes using the array to deliver light of different colors and intensity to multiple points of a mammalian brain in a 3D pattern.

16. The process of claim 15, wherein the process further comprises using the light, in conjunction with optogenetic reagents, to activate or silence neurons.

17. The process of claim 16, wherein the process further comprises delivering light to multiple locations in a three-dimensional arrangement in such a way that the color of light delivered to at least one said location differs from the color of light delivered to at least one other said location.

18. The process of claim 16, wherein the process further comprises delivering light in such a manner that the color of light delivered to a location at a particular time differs from the color of light delivered to the same location at a different time.

19. The process of claim 10, wherein the process further comprises delivering light pulses to multiple layers of tissue in a direction perpendicular to the axis.

* * * * *